(12) United States Patent
Alivisatos et al.

(10) Patent No.: US 7,534,488 B2
(45) Date of Patent: May 19, 2009

(54) GRADED CORE/SHELL SEMICONDUCTOR NANORODS AND NANOROD BARCODES

(75) Inventors: A. Paul Alivisatos, Oakland, CA (US); Erik C. Scher, San Francisco, CA (US); Liberato Manna, Palo Del Collie (IT)

(73) Assignee: The Regents of the University of California, Oakland, CA (US)

( * ) Notice: Subject to any disclaimer, the term of this patent is extended or adjusted under 35 U.S.C. 154(b) by 909 days.

(21) Appl. No.: 10/659,992

(22) Filed: Sep. 10, 2003

(65) Prior Publication Data
US 2005/0054004 A1   Mar. 10, 2005

(51) Int. Cl.
B32B 5/16 (2006.01)
(52) U.S. Cl. .................. 428/402; 428/403; 428/404; 428/405; 428/406; 428/407; 428/620; 428/621; 428/622; 428/623
(58) Field of Classification Search ......... 428/402–407, 428/620, 621, 622, 623
See application file for complete search history.

(56) References Cited

U.S. PATENT DOCUMENTS

| | | | |
|---|---|---|---|
| 4,625,071 A | 11/1986 | Delahoy et al. | |
| 5,262,357 A | 11/1993 | Alivisatos et al. | |
| 5,331,183 A | 7/1994 | Sariciftci et al. | |
| 5,350,459 A | 9/1994 | Suzuki et al. | |
| 5,350,644 A | 9/1994 | Graetzel et al. | |
| 5,454,880 A | 10/1995 | Sariciftci et al. | |
| 5,504,323 A | 4/1996 | Heeger et al. | |
| 5,505,928 A * | 4/1996 | Alivisatos et al. | 423/299 |
| 5,523,555 A | 6/1996 | Friend et al. | |
| 5,525,440 A | 6/1996 | Kay et al. | |
| 5,537,000 A | 7/1996 | Alivisatos et al. | |
| 5,670,791 A | 9/1997 | Friend et al. | |
| 5,698,048 A | 12/1997 | Friend et al. | |
| 5,751,018 A * | 5/1998 | Alivisatos et al. | 257/64 |
| 5,804,836 A | 9/1998 | Heeger et al. | |
| 5,990,479 A | 11/1999 | Weiss et al. | |
| 6,013,871 A | 1/2000 | Curtin | |
| 6,207,392 B1 | 3/2001 | Weiss et al. | |
| 6,225,198 B1 * | 5/2001 | Alivisatos et al. | 438/497 |
| 6,239,355 B1 | 5/2001 | Salafsky | |
| 6,277,740 B1 | 8/2001 | Goldstein | |
| 6,306,736 B1 | 10/2001 | Alivisatos et al. | |
| 6,322,901 B1 * | 11/2001 | Bawendi et al. | 428/548 |
| 6,423,551 B1 | 7/2002 | Weiss et al. | |
| 6,440,213 B1 | 8/2002 | Alivisatos et al. | |
| 6,607,829 B1 * | 8/2003 | Bawendi et al. | 428/403 |
| 6,788,453 B2 * | 9/2004 | Banin et al. | 359/342 |
| 2002/0006723 A1 | 1/2002 | Goldstein | |
| 2002/0016306 A1 | 2/2002 | Hutchison et al. | |

FOREIGN PATENT DOCUMENTS

WO  WO 99/25028 A1  6/1999

OTHER PUBLICATIONS

Schlamp, et al., *Journal of Applied Physics*, vol. 82, No. 11, pp. 5837-5842, (Dec. 1997).
Sirringhaus, et al., *Science*, vol. 280, pp. 1741-1744, (Jun. 1998).
Peng, et al., *Journal of the American Chemical Society*, vol. 123, pp. 183-184, (Dec. 2001).
Manna, et al., *Journal of the American Chemical Society*, vol. 122, pp. 12700-12706, (Dec. 2000).
Shaheen, et al., *Applied Physics Letters*, vol. 78, No. 6, pp. 841-843, (Feb. 2001).
Dittmer, et al., *Advanced Materials*, vol. 12, No. 17, pp. 1270-1274, (Sep. 2000).
Arango, et al., *Advanced Materials*, vol. 12, No. 22, pp. 1689-1692, (Nov. 2000).
Alivisatos, *Science*, vol. 271, pp. 933-936, (Feb. 1996).
Winiarz, et al., *Chemical Physics*, vol. 245, pp. 417-428, (Jan. 1999).
Schmidt-Mende et al., *Reports*, (Jun. 2001).
Yu, et al., *Journal of Applied Physics*, vol. 78, No. 7, pp. 4510-4515, (Oct. 1995).
Halls, et al., *Nature*, vol. 376, p. 498-500, (Aug. 1995).
Schon, et al., *Nature*, vol. 403, pp. 408-410, (Jan. 2000).
Roman, et al., *Advanced Materials*, vol. 9, No. 15, pp. 1164-1168, (Jan. 1997).
Roman, et al., *Advanced Materials*, vol. 10, No. 10, pp. 774-777, (Jan. 1998).
Granstrom, et al., *Synthetic Metals*, vol. 102, pp. 957-958, (Jan. 1999).
Gao, et al., *Advanced Materials*, vol. 10, No. 9, pp. 692-695, (Jan. 1998).
Zhang, et al., *Advanced Materials*, vol. 13, No. 24, pp. 1871-1874, (Dec. 2001).
Hiramoto, et al., *Applied Physics Letters*, vol. 73, No. 18, pp. 2627-2629, (Nov. 1998).

(Continued)

*Primary Examiner*—Leszek Kiliman
(74) *Attorney, Agent, or Firm*—Townsend and Townsend and Crew LLP

(57) ABSTRACT

Disclosed herein is a graded core/shell semiconductor nanorod having at least a first segment of a core of a Group II-VI, Group III-V or a Group IV semiconductor, a graded shell overlying the core, wherein the graded shell comprises at least two monolayers, wherein the at least two monolayers each independently comprise a Group II-VI, Group III-V or a Group IV semiconductor.

26 Claims, 7 Drawing Sheets

OTHER PUBLICATIONS

Abdou, et al., *Journal of the American Chemical Society*, vol. 119, pp. 4518-4524, (Jan. 1997).
Halls, et al., *Physical Review B*, vol. 60, No. 8, pp. 5721-5726, (Aug. 1999).
Yu, et al., *Applied Physics Letters*, vol. 64, No. 25, (Jun. 1994).
Yu, et al., *Applied Physics Letters*, vol. 64, No. 12, pp. 1540-1542, (Mar. 1994).
Tang, *Applied Physics Letters*, vol. 48, No. 2, pp. 183-185, (Jan. 1986).
Halls, et al., *Applied Physics Letters*, vol. 68, No. 22, pp. 3120-3122, (May 1996).
Park, et al., *Synthetic Metals*, vol. 79, pp. 177-181, (Jan. 1996).
Yoshino, et al., *IEEE Transactions on Electron Devices*, vol. 44, No. 8, (Aug. 1997).
Harrison, et al., *Physical Review B*, vol. 55, No. 12, pp. 7831-7849, (Mar. 1997).
Gao, et al., *Synthetic Metals*, vol. 84, pp. 979-980, (Jan. 1997).
Tada, et al., *Japanese Journal of Applied Physics*, vol. 36, Part 2, No. 3A, pp. L306-L309, (Mar. 1997).
Tada, et al., *Synthetic Metals*, vol. 85, pp. 1305-1306, (Jan. 1997).
Kohler, *Nature*, vol. 392, p. 903-906, (Apr. 1998).
Ginger, et al., *Applied Physics Letters.*, vol. 59, No. 16, pp. 10622-10629, (Apr. 1999).
Sharma, et al., *Optical Materials*, vol. 13, pp. 261-265, (Jan. 1999).
Kasam, *Journal of Materials Science*, vol. 34, pp. 5237-5242, (Jan. 1999).
Ouali, et al., "Oligo(phenylenevinylene)/Fullerene Photovoltaic Cells: Influence of Morphology", *Advanced Materials* (Jul. 1999).
Chartier et al., *Solar Energy Materials & Solar Cells*, vol. 52, pp. 413-421,.(Jan. 1998).
Greenham, et al., *Physical Review B*, vol. 54, No. 24, pp. 17628-17637, (Dec. 1996).
Peng, "High Quality Inorganic Semiconductor Nanocrystals for New Solar Cells", pp. 1-8.
Zaban et al., *Langmuir*, vol. 14, pp. 3153-3156, (May 1998).
Gratzel, *MRS Bulletin*, pp. 61-66, (Oct. 1993).
Li, et al., *Synthetic Metals*, vol. 94, pp. 273-277, (Jan. 1998).
Kavan, et al., *Journal of Physical Chemistry*, vol. 97, pp. 9493-9498, (Jun. 1993).
Nazeeruddin, et al. *Journal of the American Chemical Society*, vol. 115, pp. 6382-6390, (Jan. 1993).
Huang, et al., *Journal of Physical Chemistry B*, vol. 101, pp. 2576-2582, (Mar. 1997).
Bach, et al., *Nature*, vol. 395, pp. 583-585, (Oct. 1998).
Smestad, et al., *Journal of Chemical Education*, vol. 75, No. 6, pp. 752-756, (Jun. 1998).
Vogel, et al., *Journal of the American Chemical Society*, vol. 98, pp. 3183-3188, (Feb. 1994).
O'Regan, et al., *Nature*, vol. 353, pp. 737-740, (Oct. 1991).
Granstrom, et al., *Nature*, vol. 395, pp. 257-260, (Sep. 1998).
Marks, et al., *J. Phys.: Condens. Matter*, vol. 6, pp. 1379-1393, (Jun. 1994).
Petritsch, et at., *Solar Energy Materials & Solar Cells*, vol. 61, pp. 63-72, (Jan. 2000).
Dittmer, et al., *Solar Energy Materials & Solar Cells*, vol. 61, pp. 53-61, (Jan. 2000).
Krasnikov, et al., *Department of Polymer Chemistry, Materials Science Centre, University of Groningen: Infosheet 'Interpenetrating Morphologies for Photovoltaic Devices'*.
Halls, et al., *Synthetic Metals*, vol. 85, pp. 1307-1308, (Jan. 1997).
Roman, et al., *Advanced Materials*, "Trapping Light in Polymer Photodiodes with Soft Embossed Gratings" (Jan. 2000).
Yu, et al., *Science*, vol. 270, pp. 1789-1791, (Dec. 1995).
Huynh, "*Nanocrystal-Polymer Solar Cells*", (May 2002) Dissertation U.C. Berkeley Chemistry Department.
Ahmadi, et al., *Science*, vol. 272, pp. 1924-1926, (Jun. 1996).
Alivisatos, Journal of Physical Chemistry, vol. 100, pp. 13226-13239, (Mar. 1996).
Ataev, et al., *Tech. Phys. Lett.*, vol. 23, No. 11, pp. 842-843, (Nov. 1997).
Bandaranayake, et al., *Applied Physics Letters*, vol. 67, No. 6, pp. 831-833, (Aug. 1995).
Berman, et al., *Science*, vol. 269, pp. 515-518, (Jul. 1995).
Chang, et al., *Langmuir*, vol. 15, pp. 701-709, (Dec. 1999).
Chemseddine, et al., *Eur. J. Inorg. Chem.*, pp. 235-245, (Jan. 1999).
Chen, et al., *Chem. Mater.*, vol. 12, pp. 1516-1518, (May 2000).
Cho, *Journal of Crystal Growth*, 201-202, pp. 1-7, (Jan. 1999).
Cui, et al., *Science*, vol. 293, pp. 1289-1292, (Aug. 2001).
Dai, et al., *Chemical Physics Letters*, vol. 358, pp. 83-86, (May 2002).
Holmes, et al., *Science*, vol. 287, pp. 1471-1473, (Feb. 2000).
Hu, et al., *Accounts of Chemical Research*, vol. 32, No. 5, pp. 435-445, (Feb. 1999).
Huynh, et al., *Advanced Materials*, vol. 11, No. 11, pp. 923-927, (Nov. 1999).
Huynh, et al., *Science*, vol. 295, pp. 2425-2427, (Mar. 2002).
Ito, *Japanese Journal of Applied Physics*, vol. 37, Part 2, No. 10B, pp. L1217-L1220, (Sep. 1998).
Jin, et al., *Science*, vol. 294, pp. 1901-1903, (Nov. 2001).
Jun, et al., *Journal of the American Chemical Society*, vol. 123, pp. 5150-5151, (May 2001).
Leon, et al., *Science*, vol. 267, pp. 1966-1968, (Mar. 1995).
Li, et al., *Nature*, vol. 402, pp. 393-395, (Nov. 1999).
Lieber, *Solid State Communications*, vol. 107, No. 11, pp. 607-616, (Nov. 1998).
Liu, et al., *Physical Review Letters*, vol. 84, No. 9, pp. 1958-1961, (Feb. 2000).
Mews, et al., *Physical Review B*, vol. 53, No. 20, pp. R13 242-R13 245, (May 1996).
Murray, et al., *Journal of the American Chemical Society*, pp. 8706-8715, (Jan. 1993).
Ni, et al., *Chem. Mater.*, vol. 14, pp. 1048-1052, (Feb. 2002).
Park, et al., *Physical Review B*, vol. 49, No. 7, pp. 4485-4493, (Feb. 1994).
Park, et al., *Journal of the American Chemical Society*, vol. 122, , pp. 8581-8582, (Aug. 2000).
Paul, *Advanced Materials*, vol. 11, No. 3, pp. 191-204, (Jan. 1999).
Peng, et al., *Journal of the American Chemical Society*, vol. 120, pp. 5343-5344, (May 1998).
Peng, et al., *Journal of the American Chemical Society*, vol. 124, pp. 3343-3353, (Jan. 2002).
Peng, et al., *Nature*, vol. 404, pp. 59-61, (Mar. 2000).
Penn, et al., *Science*, vol. 281, pp. 969-971, (Aug. 1998).
Qi, et al., *Journal of Physical Chemistry B*, vol. 101, pp. 3460-3463, (Apr. 1997).
Rees, et al., *Languir*, vol. 15, pp. 1993-2002, (Feb. 1999).
Satoh, et al., *Japanese Journal of Applied Physics*, vol. 38, Part 2, No. 5B, pp. L586-L589, (May 1999).
Shevchenko, et al., *Advanced Materials*, vol. 14, No. 4, pp. 287-290, (Feb. 2002).
Smalley, et al., *Solid State Communications*, vol. 107, No. 11, pp. 597-606, (Jan. 1998).
Tanori, et al., *Langmuir*, vol. 13, pp. 639-646, (Jan. 1997).
Trentler, et al., *Science*, vol. 270, pp. 1791-1794, (Dec. 1995).
Wang, et al., *Science*, vol. 293, pp. 1455-1457, (Aug. 2001).
Yeh, et al., *Physical Review B*, vol. 45, No. 20, pp. 12 130-12 133, (May 1992).
Yeh, et al., *Physical Review B*, vol. 46, No. 16, pp. 10 086-10 097, (Oct. 1992).
Yu, et al., *The Journal of Physical Chemistry B*, vol. 101, No. 34, pp. 6661-6664, (Aug. 1997).
Zhou, et al., *Materials Research Bulletin*, vol. 34, No. 10/11, pp. 1563-1567, (Jan. 1999).
Zhou, et al., *Journal of Applied Polymer Science*, vol. 80, pp. 1520-1525, (Jan. 2001).
Cerullo, et al, *In: Summaries of Papers at the Quantum and Laser Science Conference, QELS '96. New York: IEEE*, pp. 167-168, Jun. 2-7, 1996.

\* cited by examiner

Fig 8
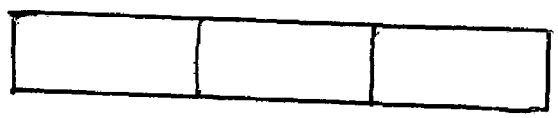
FIG 9
FIG 10
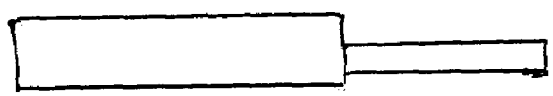

GRADED CORE/SHELL SEMICONDUCTOR NANORODS AND NANOROD BARCODES

STATEMENT AS TO RIGHTS TO INVENTIONS MADE UNDER FEDERALLY SPONSORED RESEARCH OR DEVELOPMENT

The invention described and claimed herein was made in part utilizing funds supplied by the United States Department of Energy under contract NO. DE-AC03-76SF000-98 between the United States Department of Energy and The Regents of the University of California. The government has certain rights to the invention.

PRIORITY

This application claims priority to U.S. Provisional applications 60/409,843, filed Sep. 10, 2002 and 60/409,845, filed Sep. 10, 2002, the contents of which are both incorporated herein by reference for all purposes.

BACKGROUND OF THE INVENTION

Colloidal semiconductor nanocrystals is an important field in modern nanoscale science and technology, see Bawendi, M. G.; Steigerwald, M. L.; Brus, L. E. *Annu. Rev. Phys. Chem.* 1990, 41, 477-496 and Alivisatos, A. P. *Science* 1996, 271, 933-937, the contents of both are hereby incorporated by reference in their entirety for all purposes. Among the various materials, colloidal CdSe quantum dots are undoubtedly the most studied, due to their tunable emission in the visible range, the advances in their preparation and their potential use in industrial and biomedical applications.

Recently, several advances in the synthesis of colloidal semiconductor nanocrystals have been made, allowing for size and shape control, see Peng, X. G.; Manna, L.; Yang, W. D.; Wickham, J.; Scher, E.; Kadavanich, A.; Alivisatos, A. P. *Nature* 2000, 404, 59-61 and Manna, L.; Scher, E. C.; Alivisatos, A. P. *J. Am. Chem. Soc.* 2000, 122, 12700-12706, the contents of both are hereby incorporated by reference in their entirety for all purposes. Of particular interest in this respect is the ability to obtain quantum confined wurtzite CdSe nanorods with a narrow distribution of lengths and diameters. Well-characterized samples of CdSe nanorods have become a model system to study theories of quantum confinement: for instance, it has been demonstrated, both theoretically and experimentally, that they emit linearly polarized light along the c-axis and that the degree of polarization is dependent on the aspect ratio of the particles. Semiconductor nanorods are of particular interest because of their possible applications in light emitting diodes, in low-cost photovoltaic devices, their propensity to form liquid crystalline phases and their use as barcodes for analytical purposes.

U.S. Pat. No. 6,225,198, the contents of which are hereby incorporated by reference in its entirety for all purposes discloses processes for forming Group II-VI semiconductor nanocrystals and rod-like structures by contacting the semiconductor nanocrystal precursors with a liquid media comprising a binary mixture of phosphorous-containing organic surfactants. In semiconductor quantum dots, which are nanocrystals and not the nanorods of the present invention, high emission efficiency from band-edge states is required to study in detail their electronic structure or more practically, if they are to be used as emitters in any application. Unfortunately, the band-edge emission from nanocrystals has to compete with both radiative and non-radiative decay channels, originating from surface electronic states. In colloidal nanocrystals, coating the surface of the nanocrystals with suitable organic molecules can minimize this problem. The judicious choice of a passivating agent can in fact improve the size-dependent band-edge luminescence efficiency, while preserving the solubility and processability of the particles. Unfortunately, passivation by means of organic molecules is often incomplete or reversible, exposing some regions of the surface to degradation effects such as photooxidation. In some cases, chemical degradation of the ligand molecule itself or its exchange with other ligands might lead to unstable and therefore unusable nanocrystals.

In the case of colloidal CdSe nanorods, there are two additional factors that might further reduce the luminescence from band-edge states, when compared to spherical CdSe nanocrystals. In nanorods, the surface-to-volume ratio is higher than in spheres, and this increases the occurrence of surface trap-states. In larger dots, the increased delocalization of carriers reduces the overlap of the electron and hole wavefunctions, lowering the probability of radiative recombination. The delocalization of carriers should be particularly high in a nanorod, where they are free to move throughout the length of the rod, thereby leading to reduced luminescence in nanorods. In order to efficiently and permanently remove most of the surface states of the nanocrystal, an inorganic material can be epitaxially grown on its surface, see Peng, X. G.; Schlamp, M. C.; Kadavanich, A. V.; Alivisatos, A. P. *J. Am. Chem. Soc.* 1997, 119, 7019-7029, the contents of which is hereby incorporated by reference in their entirety for all purposes.

A stringent requirement for the epitaxial growth of several monolayers of one material on the top of another is a low lattice mismatch between the two materials. If this requirement is not met, a strain accumulates in the growing layer and eventually it may be released through the formation of misfit dislocations, degrading the optical properties of the system, see for example Dabbousi, B. O.; Rodriguez Viejo, J.; Mikulec, F. V.; Heine, J. R.; Mattoussi, H.; Ober, R.; Jensen, K. F.; Bawendi, M. G. *J. Phys. Chem. B* 1997, 101, 9463-9475, the contents of which is hereby incorporated by reference in their entirety for all purposes. The preparation of a coated semiconductor nanocrystal may be found in U.S. Pat. Nos. 6,607,829 and 6,322,901 the contents of which are all incorporated by reference in their entirety for all purposes.

In the case of "spherical" colloidal CdSe nanocrystals, there are two methods of efficient inorganic passivation, one by means of a spherical layer (or shell) of ZnS, and the other by means of a shell of CdS. The choice of these materials is based on the fact that both ZnS and CdS provide a potential step for electrons and holes originating in the nanocrystals, reducing the probability for the carriers to sample the surface. Surprisingly, the requirement for a low lattice mismatch is not as stringent as for 2D systems, because the total area over which the strain accumulates is small, and the total strain energy at the interface can remain below the threshold for inducing dislocations. The extended surface of the CdSe rods has an average curvature that is intermediate between the surface of a spherical dot and that of a flat film. In addition, since CdSe nanorods can be produced with lengths ranging from a few nanometers to a hundred nanometers, the coherent growth of an epitaxial shell over a region that is much more extended than the surface of a spherical dot is more challenging. Both conditions imply that interfacial strain will play a much more important role in rods than in dots. An additional issue that must be taken into account is the solubility of the resulting particles. The shell growth must be carried out in a surfactant that provides surface accessibility for the shell material to grow, while preventing aggregation of the particles. The temperature must also be kept low enough to prevent nucleation of the shell material, while high enough that the surfactant is dynamically going on and off the nanocrystal surface allowing access to the monomers.

The art is replete with chemical and biological assays to identify a particular analyte of interest. Examples included immunoassays, fluorescence, signal amplification, nucleic acid hybridization and high throughput screening. Each of the above-described assay formats utilizes detectable labels to identify the analyte of interest. Radio-labeled molecules and compounds are frequently used to detect biological compounds both in vivo and in vitro. However, due to the inherent problems associated with the use of radioactive isotopes, non-radioactive methods of detecting biological and chemical compounds are often preferable. U.S. Pat. No. 6,274,323 (the contents of which are hereby incorporated by reference in its entirety for all purposes) discloses the use of semiconductor nanocrystals, or quantum dots in a barcode system for identification. The disadvantage of this technology is that multiple quantum dots are required to perform an assay.

SUMMARY OF THE INVENTION

The invention described herein solves the aforementioned problems with the prior art by disclosing graded core/shell semiconductor nanorods and barcode nanorods. A graded shell of larger band gap is grown around a semiconductor rod using a surfactant, in some cases tributylphosphine. Interfacial segregation is used to preferentially deposit one semiconductor material near the core, providing relaxation of the strain at the core/shell interface. The invention allows for variation of the shell thickness by growing a desired number monolayers on core nanorods ranging from aspect ratios of 2:1 to 10:1. The current invention also contemplates a photochemical annealing process which provides core/shell nanorods having increased quantum efficiencies and having stability in air under visible or UV light. The inventors have surprisingly found that by "photoannealing" or "photochemical annealing" an unexpected increase in photoluminescence QY in core-shell rods results.

In another embodiment, the present invention contemplates graded core/shell semiconductor nanorods that comprise a core of a Group II-VI, a Group III-V or a Group IV semiconductor, and a graded shell comprising the same or different Group II-VI, a Group III-V or a Group IV semiconductor.

In yet another embodiment of the present invention, there is a method for growing nanorods having alternating materials. The resultant "tails" or "nanorod barcodes" have use as detectable labels in various chemical and biological applications. The cores of the nanorod barcodes have metal or semiconductor cores.

BRIEF DESCRIPTION OF THE DRAWINGS

FIG. 8 describes semiconductor nanorod barcode having two segments, without a graded shell.

FIG. 9 describes a semiconductor nanorod barcode with three segments, without a graded shell.

FIG. 10 describes a semiconductor nanorod barcode with two segments, without a graded shell, where one segment has a smaller cross sectional area than the first segment.

DETAILED DESCRIPTION OF THE PREFERRED EMBODIMENTS

Figure 1:
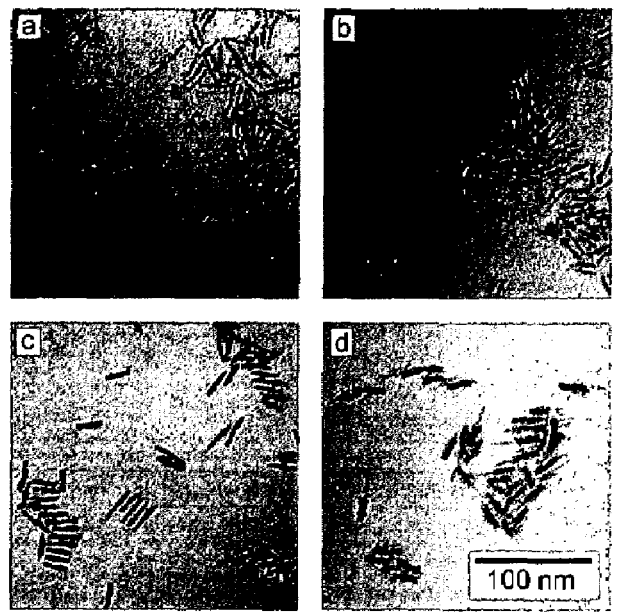
FIG. 1 shows transmission electron micrographs (TEMs) of the medium length (3.3×23 nm) CdSe core nanorods (a) and the same cores with different thickness shells of CdS/ZnS (b-d). The shell thickness is 2 monolayers (b), 4.5 monolayers (c), and 6.5 monolayers (d).

In one embodiment of the present invention there is disclosed a graded core/shell semiconductor nanorod comprising at least a first segment comprising a core comprising a Group II-VI, Group III-V or a Group IV semiconductor, a graded shell overlying the core, wherein the graded shell comprises at least two monolayers, wherein the at least two monolayers each independently comprise a Group II-VI, Group III-V or a Group IV semiconductor. In another embodiment the graded core/shell has at least three monolayers, and the monolayer closest to the core comprises a first semiconductor material, and the outermost monolayer comprises a second semiconductor material, wherein between the monolayer closest to the core and the outermost monolayer there exists a concentration gradient of the first and second semiconductor material. The number of monolayers may between two and eight or 2 and 6. In one embodiment there is a tail extending longitudinally from the core. In a preferred embodiment the core may comprise CdSe and the graded core/shell comprises CdS/ZnS. In yet another embodiment there is joined to the first segment a second segment comprising a core comprising a Group II-VI, Group III-V or a Group IV semiconductor, a graded shell overlying the core, wherein the graded shell comprises at least two monolayers, wherein the at least two monolayers each independently comprise a Group II-VI, Group III-V or a Group IV semiconductor. In a preferred embodiment the the second segment core comprises CdSe and the second segment graded shell monolayers comprise, in order, CdS/ZnS. In another embodiment the first and the second segments have different cross sectional areas. The present invention also contemplates that there is a third segment joined to the second segment and the first, second and third segments have different cross sectional areas.

In another embodiment of the invention a nanorod barcode is disclosed. The barcode comprises a first segment of a first material and a second segment of a second material joined longitudinally to said first segment; wherein the at least one of the first and second segment is capable of generating emission in response to excitation energy. In an embodiment the first and second segments comprise a nanorod core and said first and second segment cores independently comprises either a semiconductor material selected from the group consisting of Group II-VI, Group III-V and Group IV semiconductors or a metal selected from the group consisting of transition metals, oxides and nitrides thereof. The invention also contemplates that there is a third segment connected longitudinally to said first segment core, and said third segment core comprising a semiconductor material selected from the group consisting of Group II-VI, Group III-V and Group IV semiconductors. In one embodiment, the second and third segments have different cross sectional areas. In a preferred embodiment the first segment core comprises Co, and said second and third segment cores comprise CdSe. The invention contemplates that said first and second segments have different cross sectional areas. In one embodiment the at least one of said first and second segment cores have a graded shell overlying the core. In yet another embodiment both segment cores have a graded shell overlying said cores. In another embodiment there is a third segment joined longitudinally to said second segment, and said third segment comprises a semiconductor material selected from the group consisting of Group II-VI, Group III-V and Group IV semiconductors. In another embodiment the at least one of said first and second and third segment cores have a graded shell overlying the core. In another embodiment all segment cores have a graded shell overlying the cores. In yet another embodiment said first, second and third segments have different cross sectional areas.

In another embodiment of the present invention there is disclosed a method of growing a CdS/ZnS graded shell, comprising: providing a core, combining the core with at least one surfactant, heating the mixture, combining the mixture with a CdS/ZnS stock solution, wherein the core comprises a semiconductor material, and graded core/shell nanorods are produced. Preferably the core is rod shaped and comprises CdSe. In one embodiment the mixture is heated to a temperature between 100-360° C. Preferably the mixture is heated to a temperature of 160° C. Preferably the core is combined with only one surfactant. Preferably the surfactant is chosen from the group consisting of TOPO, TBP, HDA, HPA and TDPA. In one embodiment the mixture is kept at a temperature of approximately 160° for between 5 minutes and 24 hours after combining the CdS/ZnS stock solution, preferably the mixture is kept at a temperature of 160° C. for 10 minutes after combining the CdS/ZnS stock solution. Preferably the core is a shaped nanorod. More preferably the core has a tetrapod shape. In a preferred embodiment the graded core/shell nanorods are photochemically annealed, preferably using an Ar+ laser.

In another embodiment of the present invention there is disclosed a method of using a nanorod barcode to identify an element, comprising labeling at least one identifiable element with at least one nanorod barcode as described herein.

Definitions:

By "thin, medium and thick shells", it is meant that the thickness of the shells is approximately 2, 4.5 and 6.5 monolayers thick, respectively. One skilled in the art will appreciate that there is no such thing as 0.5 monolayer, and that the numbers 4.5 and 6.5 are a statistical average.

By "interfacial growth" it is meant growth of a crystal epitaxially onto another crystal forming an interface.

By "interfacial segregation" it is meant that the strain caused by the lattice mismatch of different crystals grown on top of each other causes the reorganization of the shell to form a graded shell, one where the shell naturally goes from small to larger lattice mismatch.

By "strain and induced interfacial strain" it is meant that two different crystal structures when grown epitaxially on to of one another induce strain at the interface between them.

By "tail" it is meant that segment of material extends longitudinally from one or both ends of a nanorod, or shaped nanorod. Two or more segments of materials joined together as a nanorod is also termed a "nanorod barcode". The "tails" themselves are nanorods. One skilled in the are will appreciate that for a nanorod not rod shaped, i.e. one having arms, such as tetrapods, that tails may be grown out of either or all ends of the nanorods, providing the cores are not semiconductor material.

By "joined" it is meant chemically bonded.

By "core" it is meant a shaped material that is not spherical. The invention contemplates that the core is rod-like, and may have other complex shapes as described herein. The core may comprise a semiconductor material or other metals, alloys, nitrides, oxides, etc. as defined herein.

By "transition metals" it is meant elements with atomic numbers 21-30, 39-48 and 57-80.

By "overlying said core" it is meant that the shell at least partially covers the core. In a preferred embodiment the shell covers the core entirely.

By "monolayer' it is meant a single layer of atoms in one plane. The atoms may be the same or different. The invention contemplates no limit to the amount of monolayers present, or the number of different atoms present in a monolayer. It is understood that the number of monolayers may be 9, 10, 11, 12, 13, etc. Typically the number of monolayers is between 1-8, more preferably between 1-6. The terminology where there is less than a whole number of monolayers is really a statistical average. One skilled in the art will appreciate that there is no such thing as a fraction of a monolayer.

By "CdS/ZnS", which is the terminology used to describe one example of a "graded shell", it is meant to include any number of monolayers, and compositionally this means that the first monolayer would be pure or almost pure, i.e. greater than at least 90%, preferably at least 95%, and more preferably 99% CdS, with the next layer having a percentage of Zn in the CdS, and the next monolayer (if there is one) having a higher percentage of Zn than the previous layer, and so on until the monolayer of ZnS is almost pure ZnS and practically no Cd, i.e. greater than least 90%, preferably at least 95%, and more preferably 99% pure.

By "shaped nanorods" or "nanorods having a complex shape", it is meant to include those nanorods having other than a rod shape, such as "branched" nanorods, especially those that are the subject of U.S. patent application Ser. No. 10/301,510, filed Nov. 20, 2002, entitled "Shaped Nanocrystal Particles and Methods for Making the Same", the contents of which are incorporated herein by reference in its entirety for all purposes. These include those having shapes of tetrapods, arrow, teardrop, and rods having one, two, three or more arms of varying length.

"Semiconductor nanorod" includes, for example, inorganic nanorods between about 1 nm and about 1000 nm in diameter, preferably between about 2 nm and about 50 nm, more preferably about 5 nm to about 20 nm (such as about 6, 7, 8, 9, 10, 11, 12, 13, 14, 15, 16, 17, 18, 19, or 20 nm) that includes a "core" of one or more first semiconductor materials, and which may be surrounded by a "shell" of a second semiconductor material. A semiconductor nanorod core surrounded by a semiconductor shell is referred to as a "core/shell" semiconductor nanorod. The surrounding "shell" material will preferably have a bandgap greater than the bandgap of the core material and can be chosen so to have an atomic spacing close to that of the "core" substrate. The core and/or the shell can be a semiconductor material including, but not limited to, those of the group II-VI (ZnS, ZnSe, ZnTe, CdS, CdSe, CdTe, HgS, HgSe, HgTe, MgTe and the like) and III-V (GaN, GaP, GaAs, GaSb, InN, InP, InAs, InSb, AlAs, AlP, AlSb, AlS, and the like) and IV (Ge, Si, Pb and the like) materials, and an alloy thereof, or a mixture thereof. It is also understood that the term "semiconductor nanorod" may also include those nanorods that have other than a semiconductor core, ie those with a metal core.

By "TOPO, TOP, TBP, HDA, HPA and TDPA" it is meant trioctylphosphine oxide, trioctylphosphine, tri-n-butylphosphine, hexadecylamine, hexylphosphonic acid and tetradecylphosphonic acid, respectfully.

By "method of using a nanorod barcode to identify an element" the term "element" does not strictly refer to "chemical element" as N, C, etc, but rather to any species of interest. Non limiting examples include biological entities and compounds such as cells, proteins, nucleic acids, subcellular organelles and other subcellular components. "Element" also refers to other inorganic and organic compounds such as polymers and catalysts.

It is understood that "semiconductor nanorod" may also refer to that embodiment of this invention where there are more than one semiconductor material joined longitudinally to one another. This embodiment is also referred to as "semiconductor nanorod barcode".

A "graded shell" is meant to include semiconductor nanorods that have a core and a shell that comprises at least two monolayers of a material. Typically, many monolayers are present. In a preferred embodiment, the invention contemplates a core material of CdSe, with a graded shell of CdS/ZnS. In a preferred embodiment, this invention includes at least a monolayer of CdS overlying the CdSe core and at least a monolayer of ZnS overlying the CdS layer, i.e. CdSe/CdS/ZnS. It is to be understood that there may be a small amount of S or other Group II, III, IV, V or VI element (depending on the specific materials used in the shell) in the CdSe layer. The CdS layer may consist of monolayers, preferably between 1-6, but not so limited. The monolayer closest to the CdSe layer would have a minimal concentration of S and be almost pure CdS. The monolayer closest to the outermost ZnS monolayer would be almost pure ZnS, with a small amount of Cd. The monolayer of approximate intermediate distance between the outermost ZnS monolayer and the monolayer closest to the core would have a compositional makeup of approximately 50/50% of ZnS and CdS. The instant invention contemplates that any Group II-VI or Group III-V or Group IV semiconductor may be used as materials for the graded shell. The same graded structure is present for different semiconductor materials.

By "optical pattern" it is meant the wavelength or wavelengths of light.

By "generating spectra" or "generating emission" it is meant the nanorod is capable of fluorescence or photoluminescence.

The term "barcode" as used herein refers to one or more sizes, size distributions, compositional makeup's, or combinations, of semiconductor nanorods. The present invention contemplates that nanorod barcodes may have cores of other than semiconductor materials, those cores being of metals and metal compounds. Typical metals that are to be used as a non-semiconducting core include Co, Cu, Ni, Fe, Zn, all transition metals, oxides and nitrides thereof. Each size, size distribution and/or composition of semiconductor nanorods has a characteristic emission spectrum, e.g., wavelength, intensity, FWHM, and/or fluorescent lifetime. In addition to the ability to tune the emission energy by controlling the structural properties, in particular size of the particular semiconductor nanorod, the intensities of that particular emission observed at a specific wavelength are also capable of being varied, thus increasing the potential information density provided by the semiconductor nanorod barcode system. For the purposes of the present invention, different intensities may be achieved by varying the concentrations of the particular size semiconductor nanorod attached to, embedded within or associated with an item, compound or matter of interest. The "barcode" enables the determination of the location or identity of a particular item, compound or matter of interest.

By "labeling" it is meant "linking", "conjugating", associating or bonding with the element of interest.

A semiconductor nanorod is "linked" or "conjugated" with, a specific molecule or element when the semiconductor nanorod is chemically coupled to, or associated with the molecule. The terms indicate items that are physically linked by, for example, ionic interactions, covalent chemical bonds, physical forces such van der Waals or hydrophobic interactions, encapsulation, embedding, or the like. As an example without limiting the scope of the invention, nanorods can be conjugated to molecules that can interact physically with biological compounds such as cells, proteins, nucleic acids, subcellular organelles and other subcellular components. Also, nanorods can be associated with molecules that bind nonspecifically or sequence-specifically to nucleic acids (DNA RNA). As examples without limiting the scope of the invention, such molecules include small molecules that bind to the minor groove of DNA.

The graded shell layer is particularly preferred because at the surface of the semiconductor nanorod, surface defects can result in traps for electron or holes that degrade the electrical and optical properties of the semiconductor nanorod. An insulating layer at the surface of the semiconductor nanorod provides an atomically abrupt jump in the chemical nanorods, suitable materials for the layer should have good conduction and valence band offset with respect to the semiconductor nanorod. Thus, the conduction band is desirably higher and the valence band is desirably lower than those of the semiconductor nanorod. For semiconductor nanorods that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet legions may be used. Exemplary materials include ZnS, GaN, and magnesium chalcogenides, e.g., MgS, MgSe, and MgTe. For semiconductor nanorods that emit in the near IR, materials having a band gap energy in the visible, such as CdS or CdSe, may also be used. The shell layers may include as many as eight or more monolayers of the semiconductor material.

The selection of the composition of the semiconductor nanorod, as well as the size of the semiconductor nanorod, affects the characteristic spectral emission wavelength of the semiconductor nanorod. Thus, as one of ordinary skill in the art will realize, a particular composition of a semiconductor nanorod as listed above will be selected based upon the spectral region desired. For example, semiconductor nanorods that emit energy in the visible range include, but are not limited to CdS, CdSe, CdTe, ZnSe, ZnTe, GaP, and GaAs. Semiconductor nanorods that emit energy in the near IR range include, but are not limited to, InP, InAs, InSb, PbS, and PbSe. Finally, semiconductor nanorods that emit energy in the blue to near-ultraviolet include, but are not limited to ZnS and GaN. For any particular composition selected for the semiconductor nanorods contemplated, it is possible to tune the emission to a desired wavelength by controlling the size of the particular composition of the semiconductor nanorod potential at the interface that eliminates energy states that can serve as traps for the electrons and holes. This results in higher efficiency in the luminescent process. Suitable materials for the layer include semiconductors having a higher band gap energy than the semiconductor nanorod core. In addition to having a band gap energy greater than the semiconductor.

In one non-limiting embodiment, the instant invention contemplates the growth of a CdS/ZnS graded shell on CdSe semiconductor nanorods, in the presence of a small amount of Cd precursor in trioctylphosphine oxide at low temperature (160° C.). While not wishing to be bound by any particular theory or principle, it is believed that the CdS is more likely to grow initially since its lattice mismatch with CdSe is less than that of ZnS. This layer of CdS mediates the growth of the more highly strained ZnS, but the luminescence of the core/shell nanorods is not increased very much. The shell growth is uniform and epitaxial, completely coating the CdSe core but may have defects present due to the lower growth temperature.

In one embodiment, the invention contemplates a photochemical annealing process, and the resulting nanorod has an increased luminescence efficiency of from below 1% to up to 20-25%, while preserving their solubility in a wide range of solvents.

Current synthetic techniques for nanorods and core/shell nanorods rely on a convoluted interplay of kinetic and thermodynamic factors. The inventors have determined that the large lattice mismatch between the core and shell, for example, CdSe and ZnS was preventing thicker shell growth. To remedy this, small amounts of $Cd(CH_3)_2$ were added to the stock solution to facilitate growth of a CdS layer. CdS has a lattice spacing between that of CdSe and ZnS, which decreases the overall strain in the system. In the stock solution used for this series of experiments, the Zn:Cd ratio was quite high (~8:1), in order to promote the growth of ZnS, using the CdS only as an intermediate between the CdSe and the ZnS. The Zn:S molar ratio was set higher than 1:1 to ensure a Zn rich surface. This allows the phosphine oxide, which specifically binds to metal sites, to easily coordinate the surface of the nanocrystals. Upon gradual injection of the stock solution, a color change from dark red to brown was observed. The degree of color change was dependent on the nanocrystal sample and on the amount of stock solution added. In the following experiments, the amount of stock solution injected ranged from 0.25 ml to 1.5 ml.

It is understood that the present invention contemplates graded shells on all sizes and shapes of nanorods. These include rod shaped nanorods as well as nanorods having complex shapes.

The synthetic techniques described by the present invention allow for the creation of nanorods with "tails", which consist of a nanorod of one material and a tail of another material grown out of one or both ends of the initial nanorod, as well as repeats of this structure called "nanorod barcodes". If the core is of a semiconductor material, the tail will only grow out of only one end of the rod. This is true regardless if the shape is rod-like, or other, such as tetrapods. If the core is of a metal, the tail will grow out of both ends. Metals contemplated as a core include Co, Cu, Ni, Fe, Zn, all transition metals, oxides and nitrides thereof. Since inorganic nanocrystals possess optical, electrical, magnetic, catalytic, and mechanical properties that can be widely tuned by variation of their size and shape, this invention connects these properties.

The present invention describes a systematic method for synthesizing nanorod barcodes based on conditions which favor growth of the 001 or 00-1 faces of the hexagonal crystal structure. There is no limit to the number of sections in a nanorod barcode, but preferably the number is small, for example 2-3. But nanorod barcodes with sections of 4, 5, 6, 7 and more are possible. The sections of the nanorod barcode are bonded together with chemical bonds, either covalent or ionic bonds. The materials contemplated for the different sections of the nanorod barcode are the same as those for the core material or the shell material, except that the core in a nanorod barcode is may be other than a semiconductor.

The growth of a tail of a semiconductor material, such as ZnS out of one end of the nanorods also provides evidence of the intense strain present in these particles. After 5-6 monolayers of shell are grown the strain induced by the lattice mismatch is too great to continue regular shell growth. To relieve this strain a tail grows out of one end of the rod, ZnS in this example. Since the tail consists solely of shell material, it only feels the strain for the few monolayers that connect it to the body of the rod. The rest of the tail has the unstrained lattice parameters of ZnS. A similar situation occurs for the lumps that grow on the other faces of the rod (the reason that a tail only grows out of one side is due to the lack of inversion symmetry in the wurtzite structure and the higher energy of the 001 face relative to the others. This is observed not only in the TEM but also in the XRD pattern of the thick shell samples (FIG. 4e). In that pattern some small very broad peaks of ZnS are observed on top of the core/shell diffraction.

These peaks result from the tails and lumps that are diffracting as if they were small isolated domains of ZnS.

Figure 11:
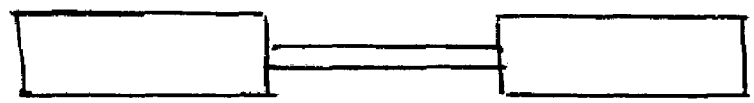
FIG. 11 describes a semiconductor nanorod barcode with three segments, each having a different cross sectional area.
Figure 12:
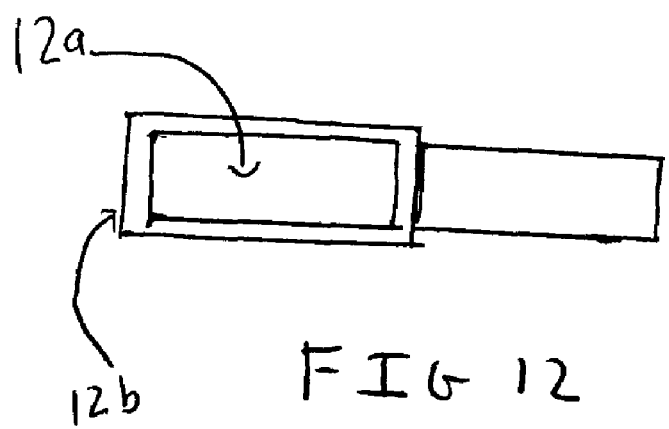
FIG. 12 describes a semiconductor nanorod barcode with two segments having a graded shell on one of the segments.
Figure 13:
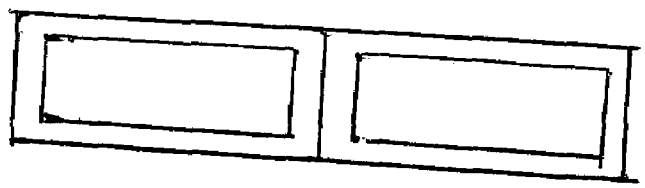
FIG. 13 describes a semiconductor nanorod barcode with two segments, both having a graded shell.
Figure 14:
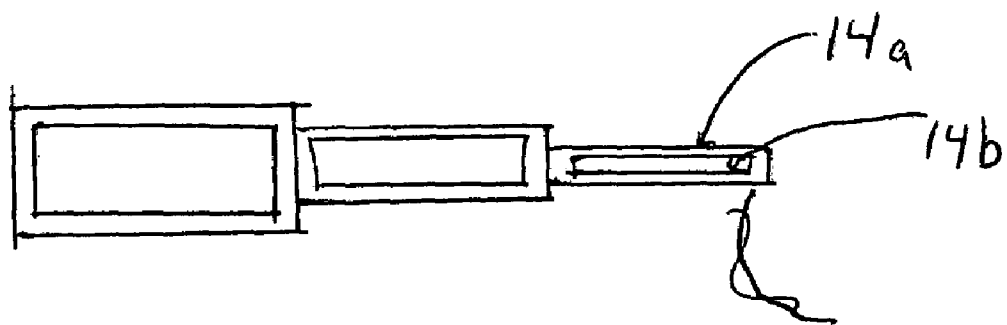
FIG. 14 describes a semiconductor nanorod with a graded shell, having three segments, each having a different cross sectional area.
Figure 15:
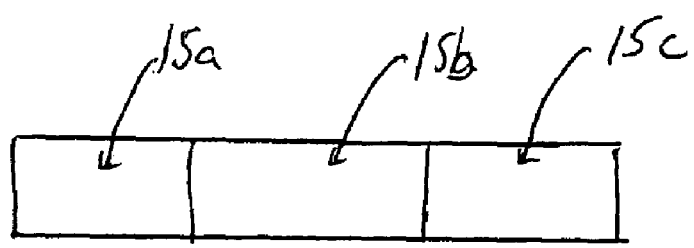
FIG. 15 describes a nanorod barcode where one segment is a metal, and the segment grown out of both ends comprises a semiconductor material.

FIGS. 8-15 describe embodiments of nanorod barcodes in accordance with the present invention. The cross sectional area of barcodes and also semiconductor nanorods is approximately hexagonal or circular. FIG. 10 shows an embodiment where the cross sectional area of the tail or second segment is smaller than that of the first segment. FIG. 11 and FIG. 14 describe embodiments where there are three segments, each having different cross sectional areas. One skilled in the art will appreciate that by tailoring the growth parameters one can manipulate the cross sectional areas of the segments and thus tune the resulting emissions. FIG. 12a is the core in one embodiment of the present invention and FIG. 12b is the graded shell. FIG. 14a shows the graded shell in one embodiment of the present invention, and FIG. 14b shows the core. FIG. 15a and FIG. 15c describe semiconductor segments joined to a metal core (FIG. 15b).

A unique optical pattern or barcode can be detected when a nanorod is functionalized or unfuctionalized with a particular ligand, or bound to a particular target molecule or target molecules. When the nanorod encoded with an optical pattern or barcode is introduced into a biological or other system, it can be located and tracked using a variety of detection devices, usually optical detection devices. For example, a semiconductor nanorod barcode bound to a cell can be used to track the movement of a cell in a biological fluid (e.g., blood, serum, lymph, semen, vaginal fluid).

The present invention contemplates two methods for synthesis of nanorod-barcodes. Both involve synthesizing a nanorod of one material and then growing an additional material out of one or both ends of the existing rod. This can be done by injecting precursors of the second material in the same surfactant mixture as the first nanorods were grown in, thereby using these surfactants to control growth. Another method is to remove preform growth in a surfactant that does not promote shape control, but to use the inherent lattice mismatch between two materials to have strain induced rod growth out of one end of the initial nanorod. This procedure can be performed for any crystal with a hexagonal structure whose lattice mismatch is not so large as to prevent any epitaxial growth on the initial nanorod. This procedure is repeated so that it is possible to add different materials to create a nanorod barcode.

The graded semiconductor nanorods and barcodes of the present invention are, optionally, surrounded by a "coat" of an organic capping agent. Thus the nanorod and/or barcode may be linked, conjugated, associated with a specific molecule, when the semiconductor nanorod is chemically coupled or associated with the specific molecule. The organic capping agent may be any number of materials, but has an affinity for the semiconductor nanorod surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanorod homogeneously into a chosen solvent, functionality, binding properties, or the like. In addition, the coat can be used to tailor the optical properties of the semiconductor nanorod.

EXAMPLES

The examples provided herein are provided as examples and not limitations, wherein a number of modifications of the exemplified process are contemplated and within the scope of the present invention.

I. Materials. Dimethylcadmium ($Cd(CH_3)_2$, 97%) and tri-n-butylphosphine ($C_{12}H_{27}P$ or TBP, 99%) were purchased from Strem. $Cd(CH_3)_2$ was vacuum transferred and stored at −35° C. under argon. Selenium (Se) (99.999%), tri-n-octylphosphine oxide ($C_{24}H_{51}OP$ or TOPO, 99%), diethylzinc ($C_4H_{10}Zn$, or $Et_2Zn$, 1.0 M solution in heptane) and hexamethyldisilathiane ($C_6H_{18}Si_2S$ or $(TMS)_2S$) were purchased from Aldrich. Hexylphosphonic acid ($C_6H_{15}O_3P$ or HPA 99%) was purchased from Organometallics Inc., and tetradecylphosphonic acid ($C_{14}H_{31}O_3P$ or TDPA, 98%) was purchased from Alfa. All solvents used were anhydrous, purchased from Aldrich and used without any further purification.

II. Stock solutions. Stock solutions were prepared in a dry box under Ar and then placed in a refrigerator at −20° C. For the synthesis of CdSe nanorods, we prepared the solution for each precursor separately. For the Se precursor, selenium powder was dissolved in TBP (concentration of Se 7.79% by weight). For the Cd precursor, $Cd(CH_3)_2$ was dissolved in TBP (concentration of Cd 32.29% by weight). The stock solution for the ZnS shell was prepared by dissolving 152 mg of $(TMS)_2S$ and 0.63 g of the $Et_2Zn$ solution in 4.1 g of TBP. In this solution the Zn:S molar ratio is 1:1. The stock solution for the CdS/ZnS graded shell was prepared by mixing 0.5 g of the $Et_2Zn$ solution, 37 milligrams of a solution of $Cd(CH_3)_2$ in TBP (32.29% by weight) and 76 mg of $(TMS)_2S$. The resulting solution was then diluted in 2.05 g of TBP. In this solution the Zn:Cd:S molar ratio is 1:0.12:0.63.

III. Synthesis of CdSe Rods. All manipulations were performed using standard air-free techniques, unless otherwise stated. In a typical synthesis, a mixture of HPA, TDPA and TOPO[20] was degassed at 120° C. for 1 hour in a 50 ml 3-neck flask connected to a Liebig condenser, after which 0.5 g of the Cd precursor solution was added drop wise. The resulting mixture was then heated to 360° C. and 2.5 g of the Se precursor solution was quickly injected. After injection, the temperature dropped to 290° C. and was maintained at this level throughout the synthesis. When desired, the synthesis was stopped by removing the heating mantle and by rapidly cooling the flask. In the present series of experiments, we prepared 4 samples of CdSe rods of different lengths and aspect ratios by varying the relative concentration of TOPO:HPA:TDPA and the growth time. The details are reported in Table 1.

After cooling the solution to 50° C., 4.0 ml of methanol was added to precipitate the rods from the solution. This suspension was then transferred to a dry box, where it was centrifuged and the precipitate was washed three times with methanol. The final precipitate was then dried under Ar and stored in the dry box. Due to the high degree of uniformity of the rods that this synthesis procedure yields, no further size selective precipitation was carried out on any samples.

IV. Epitaxial growth of CdS/ZnS graded shell. 5 grams of TOPO was placed into a 50-ml 3-neck flask, pumped under vacuum at 120° C. for 20 minutes and then cooled to 60° C. Ten mg of dry nanorods were dissolved in 2.0 ml of chloroform. This solution was removed from the glove-box and injected into the TOPO solution at 60° C. The chloroform was removed by pumping the mixture under vacuum for 20 minutes. The temperature of the mixture was raised to 160° C. Depending on the desired thickness of the shell, a given amount (see Table 2) of the CdS/ZnS stock solution was loaded into a syringe and injected dropwise into the flask. A typical injection rate for this series of experiments was around 0.1 ml/min. After the injection was completed, the solution was kept at 160° C. for 10 minutes. During this time the shell growth was completed. The temperature in the flask was then lowered to 40° C. and 3.0 ml of octanol was added to quench the unreacted precursors. The resulting solution was immediately transferred under Ar into the glove box and stored in the dark.

V. Precipitation and Re-Dissolution of Core/Shell Rods.

The solution of nanocrystals in TOPO/TBP/octanol was stable, optically clear, and no precipitate was observed even several months after the synthesis. Addition of methanol to this solution caused the precipitation of the nanocrystals, which could then be easily redissolved in solvents such as chloroform, toluene, or tetrahydrofuran. There were a few cases in which the core/shells did not redissolve. To avoid this problem, we found it was very effective to add a small amount (1 mg/ml) of a phosphonic acid, such as hexylphosphonic (HPA) acid, or of an amine such as hexadecylamine (HDA). In this case, after methanol was added, the solution immediately turned turbid and the collected precipitate could then be readily redissolved. Solubility problems were also encountered when a precipitate (obtained without the addition of HPA or HDA) was washed several times with methanol. Here the addition of HPA or HDA to the solvent caused the immediate redissolution of the particles. Henceforth we will call these samples 'HPA-capped' and 'HDA-capped' nanorods, respectively. This is to distinguish them from samples of nanorods precipitated and redissolved without the assistance of additional surfactants, which will be called 'TOPO-capped' nanorods [45,46]. In addition, we will call 'raw nanorods' the samples obtained by simply diluting in chloroform the original solution of nanocrystals in TOPO/TBP/octanol, without any precipitation or redissolution procedures.

VI. Photochemical Shell Annealing. Laser irradiation experiments to photochemically anneal the shells were carried out by exposing a 1 cm path-length quartz cuvette filled with a diluted solution of CdSe nanorods or CdSe/CdS/ZnS core/shell nanorods to a continuous Ar$^+$ laser (Lexel 95 ion laser, Lexel Laser, Inc.). The power of the laser was tuned between 50 and 120 mW, depending on the particular experiment. The 457.9 nm and the 514.5 nm line were alternatively used as excitation lines. The laser spot on the sample had a diameter of approximately 1 cm. The number of nanoparticles in the cuvette was estimated by evaluating the average weight of a single nanorod, and the total amount of CdSe in the solution. By measuring the laser power absorbed by the nanocrystal solution it is possible to calculate the average number of photons absorbed by each particle per second of exposure to the laser light.

VII. Preparation of a two segment nanorod barcode. Described is the growth of ZnS tail on CdSe nanorod. 5 grams of TOPO was placed into a 50-ml 3-neck flask, pumped under vacuum at 120° C. for 20 minutes and then cooled to 70° C. 20 mg of dry nanorods were dissolved in 2.0 ml of chloroform. This solution was removed from the glove-box and injected into the TOPO solution at 70° C. The chloroform was removed by pumping the mixture under vacuum for 20 minutes. The temperature of the mixture was raised to 160° C. After 1 hour at 160 C., 0.5 mL of ZnS stock solution was loaded into a syringe and injected dropwise into the flask. A typical injection rate for this series of experiments was around 0.1 ml/min. After injection this process was repeated until a total of 2.5 mL ZnS stock solution was injected into the flask (in another example we also used 4.0 mL of ZnS stock solution). After the injection was completed, the solution was kept at 160° C. for 10 minutes. During this time the tail growth was completed. The temperature in the flask was then lowered to 40° C. and 3.0 ml of methanol was added to quench the unreacted precursors. The resulting solution was immediately transferred under Ar into the glove box and stored in the dark.

VIII. Preparation of a two segment nanorod barcode with a graded shell. Described is the growth of ZnS tail on CdSe nanorod with graded CdS/ZnS shell. 5 grams of TOPO was placed into a 50-ml 3-neck flask, pumped under vacuum at 120° C. for 20 minutes and then cooled to 60° C. Ten mg of dry nanorods were dissolved in 2.0 ml of chloroform. This solution was removed from the glove-box and injected into the TOPO solution at 60° C. The chloroform was removed by pumping the mixture under vacuum for 20 minutes. The temperature of the mixture was raised to 160° C. After 1 hour at 160 C., 1.5 mL of the CdS/ZnS stock solution was loaded into a syringe and injected dropwise into the flask. A typical injection rate for this series of experiments was around 0.1 ml/min. After the injection was completed, the solution was kept at 160° C. for 10 minutes. During this time the shell growth was completed. The temperature in the flask was then lowered to 40° C. and 3.0 ml of octanol was added to quench the unreacted precursors. The resulting solution was immediately transferred under Ar into the glove box and stored in the dark. One skilled in the art will appreciate that additional segments may be added by repeating the growth process.

IX. Preparation of a two segment nanorod barcode with a metal core. Growth of ZnS tail on Co nanorod. 5 grams of TOPO may be placed into a 50-ml 3-neck flask, pumped under vacuum at 120° C. for 20 minutes and then cooled to 60° C. 20 mg of dry Co nanorods are dissolved in 2.0 ml of chloroform. This solution may then be removed from the glove-box and injected into the TOPO solution at 60° C. The chloroform may then be removed by pumping the mixture under vacuum for 20 minutes. The temperature of the mixture can be raised to 160° C. After 1 hour at 160 C., 1.5 mL of the ZnS stock solution should be loaded into a syringe and injected dropwise into the flask. A typical injection rate for this series of experiments is around 0.1 ml/min. After the injection was completed, the solution can be kept at 160° C. for 10 minutes. During this time the tail growth should be completed. The temperature in the flask will then be lowered to 40° C. and 3.0 ml of methanol is added to quench the unreacted precursors. The resulting solution is immediately transferred under Ar into the glove box and stored in the dark.

X. Characterization of Samples. All sampling procedures for the optical characterization of the samples were carried out under Ar unless otherwise stated. In the case of CdSe nanorod cores, a small amount of sample (~0.2 ml) was removed via syringe from the flask before the shell growth. In the case of core-shell nanorods, a small amount of the final solution stored in the dry box (~0.2 ml) was used: depending on the particular experiment, this solution was processed according to one of the procedures described in the previous section. The sample was diluted to an optical density of between 0.1 and 0.25 by addition of anhydrous chloroform in a glove box.

A. UV-Vis Absorption Spectroscopy. Absorption spectra were measured using a Hewlett Packard 8453 UV-visible diode array spectrometer equipped with a deuterium lamp having a resolution of 1.0 nm.

B. Photoluminescence spectroscopy. Photoluminescence (PL) spectra were recorded on a Spex 1681 0.22 m/0.34 m spectrometer. PL quantum efficiencies of the nanorods in chloroform were calculated by comparing their integrated emission to that of a solution of Rhodamine 6G in methanol. Optical densities of all solutions were adjusted to between 0.1 and 0.25 at the excitation wavelength to avoid re-absorption effects. The excitation wavelength used for all measurements was 480 nm. Emission spectra were corrected for the wavelength dependent response of the photomultiplier tube and for the refractive indexes of methanol and chloroform.

C. Transmission Electron Microscopy. Nanocrystal size, morphology and structure were measured via TEM. At the National Center for Electron Microscopy at Lawrence Berkeley National Laboratory, a Topcon EM002B electron microscope was used. The microscope was operated at an accelerating voltage of 120 kV. At the UC-Berkeley Electron Microscope Lab, a FEI Tecnai 12 was used with an operating voltage of 120 kV.

Nanocrystals were deposited from dilute solution onto a 3-4 nm thick film of amorphous carbon supported by 400 mesh copper grids (purchased from Ted Pella). One drop of nanocrystal solution in chloroform was deposited onto the grid and evaporated.

Structural determination was accomplished using high resolution TEM (HRTEM) at 550,000 times magnification. Average sizes and morphologies were measured at 140,000 times magnification, calibrated using known crystal lattice spacings. Average lengths and shape distributions were determined by counting at least 200 nanocrystals per sample for statistical purposes.

D. EDX. Energy dispersive X-ray Spectroscopy (EDX) was performed using a Philips CM200/FEG at the National Center for Electron Microscopy at Lawrence Berkeley National Laboratory. This microscope was operated at an accelerating voltage of 200 kV using an Oxford Model 6767 energy dispersive X-ray detector with an energy resolution of 1.36 eV for Mn K$\alpha$ radiation. Between twenty and one hundred nanorods were used per scan and at least 10 scans were taken per sample. The average scan time was between 20 and 40 minutes. For composition determination, scans times of the same length were used, and EDX scans were normalized to the Se K$\alpha$ line.

E. Powder X-ray Diffraction. Powder X-ray diffraction was performed on a Bruker-AXS D8 general area detector diffraction system (GADDS), using Co K$\alpha$ radiation (1.79026 Å). Two-dimensional patterns were angle integrated to obtain the patterns displayed. The instrument resolution is 0.07° in 2$\theta$ and the accumulation time for each frame of each sample was 20 minutes. Three frames were taken per sample, centered at 2$\theta$ angles of 25°, 40°, and 55°, and at $\Omega$ angles of 12.5°, 20°, and 27.5° respectively. XRD samples were prepared by evaporating a concentrated nanocrystal solution on a quartz plate. Prior to the measurements, the samples were washed with methanol to remove excess organic material and then dried. All Peaks were fit using commercial software (PeakFit™ v4) utilizing a Gaussian*Lorentzian peak shape.

Figure 2:
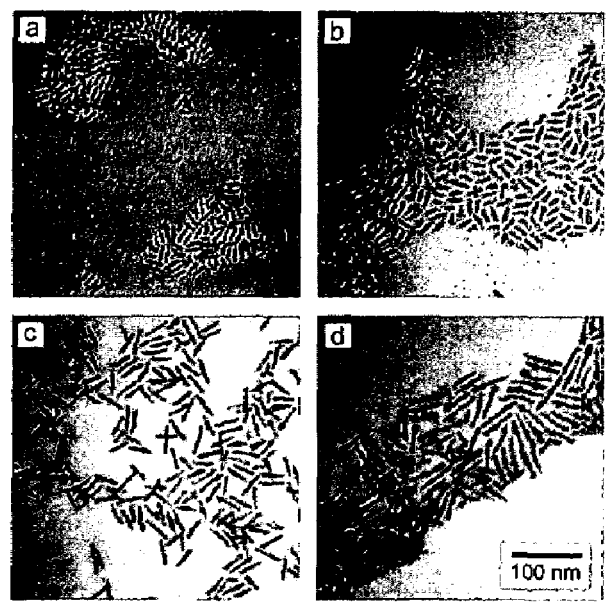
FIG. 2 shows transmission electron micrographs (TEMs) of the short (5.0×18 nm) CdSe core nanorods (a) and the same cores with a CdS/ZnS shell (b). TEMs of the long (4.5×36 nm) CdSe core nanorods (c) and the same cores with a CdS/ZnS shell (d).

II. Structural Characterization. The invention contemplates that the thickness of the graded shell can be controlled by the amount of precursor combined; preferably injection is used. Several techniques are used to monitor and characterize the shell's thickness, structure, crystallinity, and composition. FIG. 1 shows low resolution TEM images of a CdSe core nanorod (3.3×22.8 nm) (a), the same cores with a thin shell (b), a medium shell (c), and a thick shell (d). In these images one can see the increase in diameter of the nanorods from 3.3 nm in the cores to 4.4 nm in the thin shell sample, 6.0 nm in the medium shell sample, 7.3 nm in the thick shell sample. This corresponds to growing roughly 2, 4.5, and 6.5 monolayers of CdS/ZnS shell for the thin, medium, and thick shell samples respectively. The shell is observed to be very regular and conform to the shape of the underlying CdSe core as long as the shell is less than 5-6 monolayers thick. This is true not only for the medium length rods shown in FIG. 1, but is observed to be independent of aspect ratio as seen in FIG. 2. The shell growth seems to improve the overall regularity of the rods in that they seem to be straighter than the cores themselves (the irregularities in the cores are caused by zinc blende stacking faults in them).

FIG. 1d, shows a tail is observed to grow straight out of one end of the rods and the overall surface of the rods becomes rough. It is important to note that separate nuclei of CdS or ZnS particles were not observed via TEM in any of our samples. Thus, only shells are grown, and not separate nanorods or nanocrystals.

Figure 3:
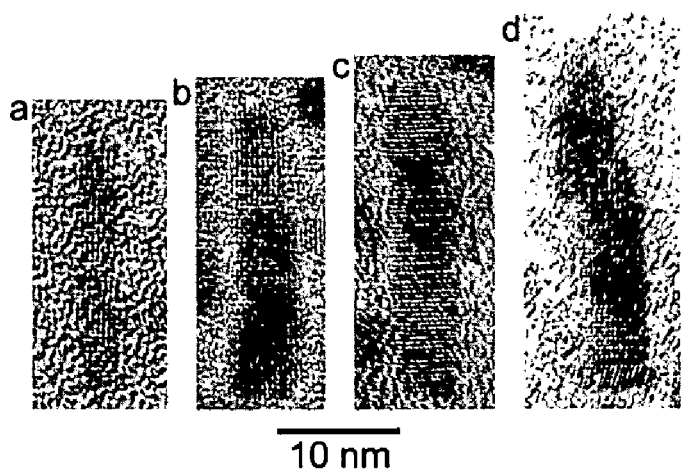
FIG. 3 shows high resolution transmission electron micrographs (HRTEMs) of the medium length (3.3×23 nm) CdSe core nanorods (a) and the same cores with different thickness shells of CdS/ZnS (b-d). The shell growth is epitaxial with fringes going through both core and shell. The shell growth is also regular except for the thickest sample (d) where the strain of the ZnS becomes too great and is relieved by irregular growth of ZnS on the shell.

In addition to the above TEM, HRTEM and XRD were used to determine the structure and crystallinity of the core/shell structures. In FIG. 3, the HRTEM images of the medium length nanorod cores (a), the same cores with a thin shell (b), medium shell (c), and thick shell (d) of CdS/ZnS are shown. The lattice fringes are continuous through both the core and shell implying epitaxial growth of the shell. There were no obvious stacking faults or defects observed at the interface of core and shell. In addition, the core and shell both have a wurtzite structure and they increase in both diameter and length as the shell thickness increases, although the length increases slightly faster than the diameter. The thickest shell samples, where the growth of a ZnS tail is observed, are more difficult to image in the HRTEM. At low magnifications, with a large beam spot size, the thin tails can be clearly observed (FIG. 1d), but when the spot size is decreased at higher magnifications (~550 kx) the tails are damaged by the beam faster than an image can be taken.

Figure 4:
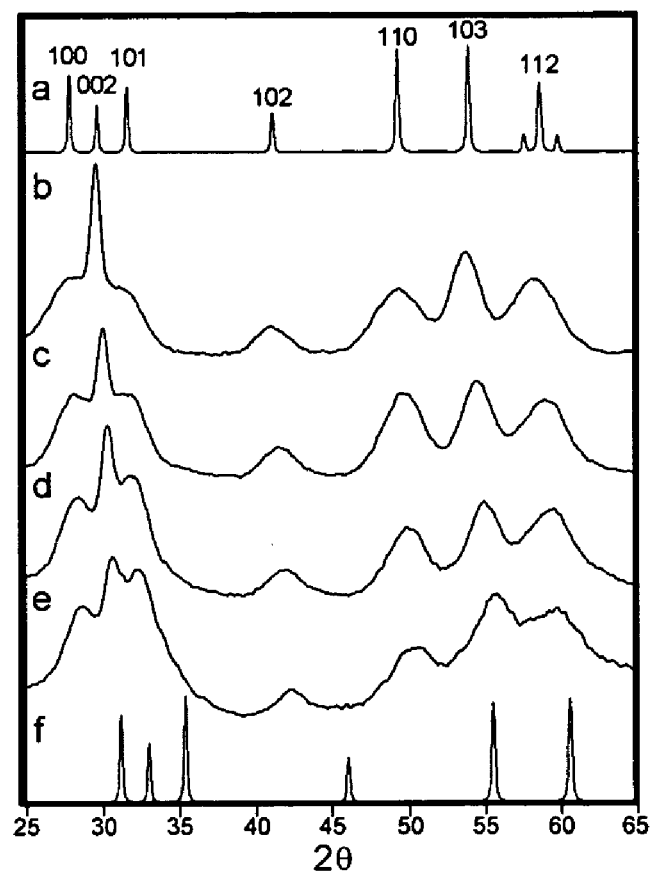
FIG. 4 shows powder x-ray diffraction (XRD) patterns of the medium length (3.3×23 nm) nanorod cores (b) and core/shells (c-e). The bulk XRD pattern of CdSe (a) and ZnS (f) are given for reference. The initial XRD pattern of the CdSe core nanorods (b) match the peak positions of bulk CdSe but the intensities are different. The 002 peak is very narrow and more intense than the other peaks because of the extended domain along the c-axis of the nanorods. In the thin (c) and medium (d) shell samples all of the peaks shift and the intensity of the 002 peak decreases relative to the other peaks. In addition to following the aforementioned trends, the thick shell sample (e) displays some small broad peaks corresponding to the ZnS growths and tails observed on them in the TEM.

Powder X-ray diffraction patterns of the same samples are shown in FIG. 4. The bulk pattern of CdSe (FIG. 4a) matches exactly that of the CdSe nanorod cores with the exception of the relative intensities of the peaks. The sharp 002 peak (29.6° 2$\theta$) results from the extended crystalline domain along the c-axis of the wurtzite lattice. As the shell is grown and its thickness increases, the diffraction peaks shift towards smaller d-spacings (larger 2$\theta$). This means that the growth of the CdS/ZnS shell is compressing the lattice planes in the CdSe core and that the compression increases as a function of shell thickness. Since a CdSe rod is an anisotropic system (in both crystal structure and shape), we should expect this compression to have a different effect on the various families of planes of the crystal. The shifts of different diffraction peaks in samples with increasingly thicker shells are shown in Table 3.

The diffraction patterns from the thin and medium thickness shell samples show that, apart from the aforementioned shifts, the peak widths are almost unchanged as compared to the core spectrum and that no additional peaks are present. In the thickest sample though, the peaks have broadened significantly and there may be small broad diffraction peaks that overlap with the ZnS bulk peaks (FIG. 4f). Once tails have begun growing on the rods, they diffract as if they were small domains of isolated ZnS. Due to Debye-Scherrer broadening, they are observed as very broad peaks with low intensity.

Figure 5:
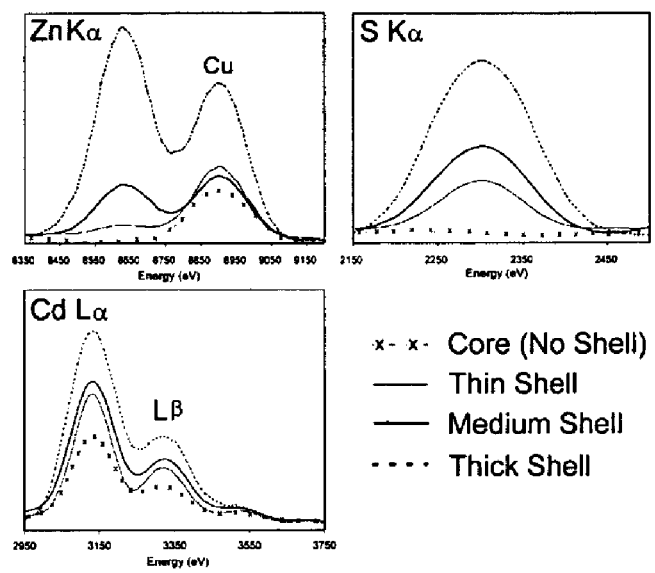
FIG. 5 shows energy dispersive X-ray (EDX) spectra of the medium length (3.3×23 nm) nanorod cores and core/shells. The Se Kα spectrum is not shown as it was used for normalization of all the samples and it does not differ between them. The Cu Kα line was subtracted when calculating the Zn Kα area. It is very clear that there is no Zn or S in the core nanorods. The amount of these elements increases as a function of shell thickness. The Cd L lines are present in the initial CdSe core sample but also increase as a function of shell thickness due to the growth of CdS in the shell.

To determine the shell composition EDX spectroscopy was used. Again, the same four samples characterized by TEM, HRTEM, and XRD were analyzed. All of the spectra were normalized to the Se K$\alpha$ line since the amount of Se in the cores and core/shells remains constant. The lines used are shown in FIG. 5. It is clear that there is no Zn or S in the CdSe core nanorods. As the shell thickness increases the amount of these elements present in the shell also increases. The Cu line is due to scattering in the microscope off the Cu TEM grid and was subtracted when determining the area of the Zn K$\alpha$ line. Since we are also adding Cd, the amount of Cd also increases with increasing shell thickness as seen in the Cd L$\alpha$ and L$\beta$ spectra. Combining the EDX data with the sizes collected via TEM the composition of the shell was determined as a function of shell thickness. CdS makes up 35% of the shell in the thin shell sample, 22% of the shell in the medium shell sample, and 22% of the shell in the thick shell sample. Since the thin shell sample has slightly less than two monolayers of shell grown on it, this corresponds to about ⅔ of a monolayer of CdS, the remainder being ZnS. As the thickness increases, the CdS continues to grow, but the ratio of Zn:Cd increases as seen in Table 2.

III. Optical Characterization and Photochemical Annealing.

The significant red shift in the absorption and emission spectra from core/shell samples also confirms that a relevant percentage of the shell is composed of CdS. Given the small energy difference between the bottom of conduction bands in CdSe and in CdS (0.2 eV in the bulk limit), the photo-generated electrons in colloidal CdSe/CdS dots can easily tunnel from the CdSe cores into the CdS shell (the core electrons have to overcome a potential step of 0.55 eV). When the thickness of the CdS shell increases, the absorption and luminescence spectra of CdSe/CdS dots shift to lower energies, since the confinement energy for the electrons is lower. This effect is less remarkable in CdSe/ZnS dots, where the potential barrier for both carriers to tunnel from the CdSe cores into the ZnS shell is approximately 0.9 eV but a red shift is still expected.

Figure 6:
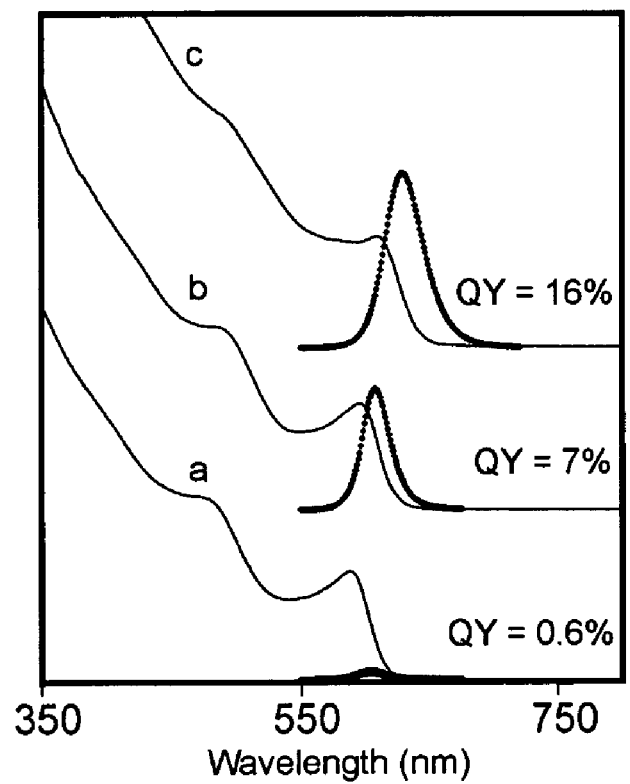
FIG. 6 shows absorption spectra (solid line) of medium length (3.3×21 nm) CdSe core nanorods (a) and thin (b) and medium (c) core/shell samples. Photoluminescence (PL) spectra (broken line) of the same samples after photoannealing. The absorption spectra do not change upon photoannealing.

FIG. 6 shows the absorption spectra (solid line) of CdSe core nanorods, and the same cores with two different thickness shells. The solutions were 'raw', as described in the paragraph V of the, experimental section. In the core-shell samples there is a progressive red shift in the spectral features, with respect to the starting CdSe cores, as the thickness of the shell increases. This suggests that CdS is included in the shell, since a less remarkable shift would be expected from a core-shell system with only ZnS in the shell. The cores had a luminescence quantum yield (QY) lower than 1%, the thin shell sample had a QY of 4%, and the QY of the medium shell sample was again less than 1%.

FIG. 6 also shows the emission spectra of the three samples (dotted lines) after exposure to laser light for 8 hours (The exposure time of these samples was 20 hours on average. The exciting wavelength was 514.5 nm, the laser power was approximately 80 mW and the optical density of all solutions was 0.2 at 480 nm. The QY from the thin shell sample increased to 7%, whereas the QY from the medium shell sample increased to 16%. Further exposure to laser light did not affect the QY from the core/shell samples. On the other hand, the same laser treatment on the CdSe cores did not significantly increase their QY. In fact their luminescence either remained constant or decreased during laser irradiation. In all samples, the laser treatment did not cause any relevant spectral shift in absorption or luminescence, or any change in the optical density of the nanocrystal solutions: this rules out any possibility that the shell grew or shrank during laser illumination. In addition, TEM, HRTEM, and XRD were carried out on samples before and after illumination. No noticeable shape change was observed.

Figure 7:
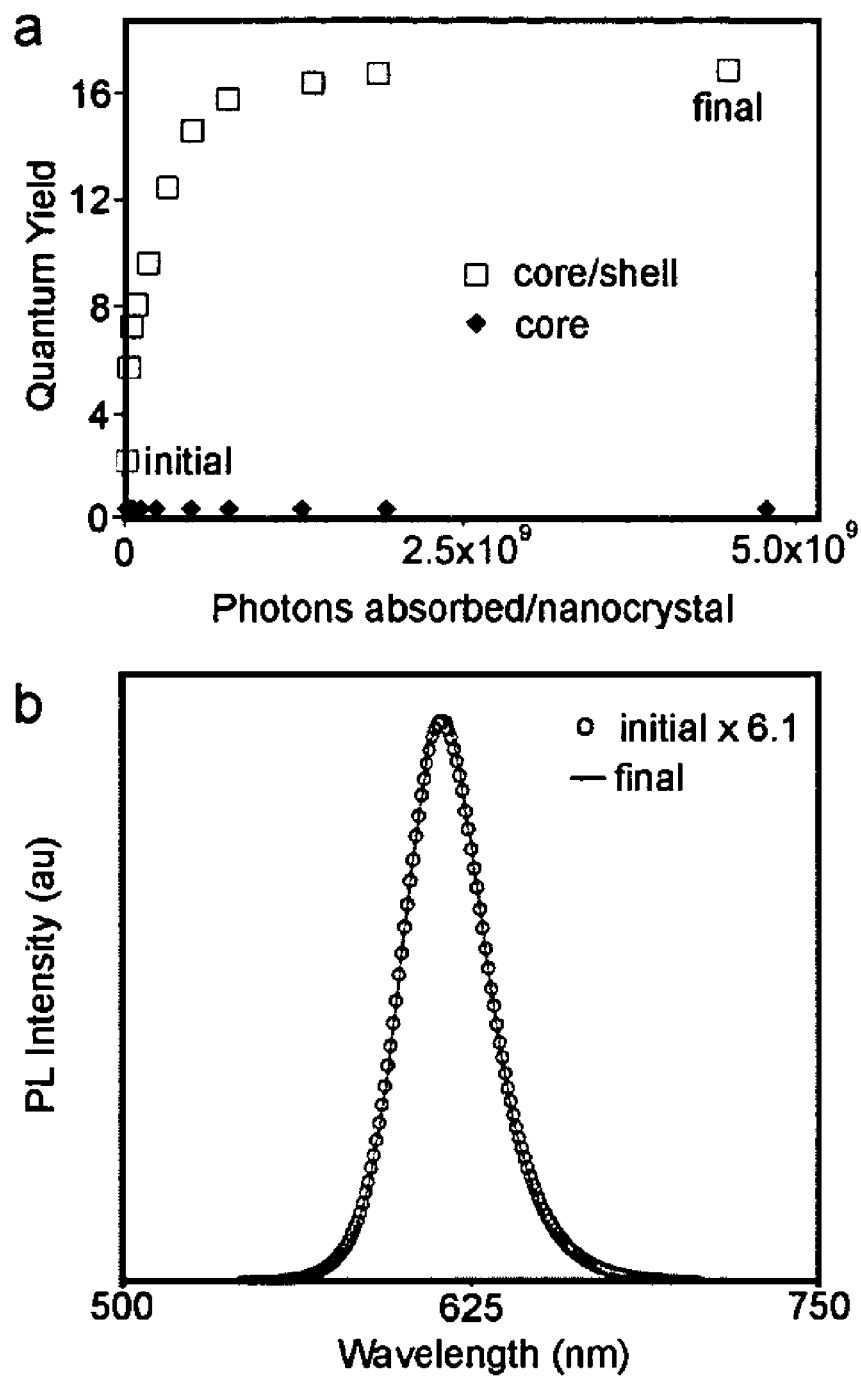
FIG. 7 shows QY of medium length (3.3×21 nm) CdSe core nanorods (♦) and medium core/shell (□) samples as a function of photons absorbed/nanocrystal (a). The cores do not change significantly with time, but the core/shell's QY increases significantly after absorbing ~$10^9$ photons/nanorod and then remains constant. Two PL spectra from the same core/shell sample are shown in (b). The initial, non-photoannealed sample (o) was multiplied by 6.12 to match the intensity of the final photoannealed sample (–). There are no noticeable changes in the peak shape, peak maximum, or full width half max after photoannealing the sample.

An increase in luminescence was observed in all core/shell samples that were photoannealed. Solutions of non-annealed core/shell rods kept under dark had low QY, even several weeks after the synthesis. After photoannealing for a few hours, their QY increased without any spectral shift. FIG. 7a shows the measured QY for a CdSe core sample and core/shell as a function of the average number of photons absorbed per particle. The core/shell sample was raw[48]. The nanorods in the CdSe core sample had a length of 21 nm and a diameter of 3.3 nm. In the core/shell sample, the ZnS shell was 2.5 monolayers thick. The core/shell sample underwent photochemical annealing as its QY started from 3% and saturated at 17%, whereas the QY from the core sample remains less than 1%.

To check the influence of the post-synthesis treatment on the photochemical annealing, the above experiments were repeated on the same core/shell sample, but cleaned according to the procedures described in the paragraph V of the experimental section. Three additional samples were then prepared from the original TOPO/TBP/octanol solution: TOPO-capped, HPA-capped, and HDA-capped core/shell. All these samples displayed quantum yield enhancement following photochemical annealing, although the HDA-capped sample reached the highest QY (it started at 4% and increased to 21%), the HPA-capped sample experienced the lowest increase in QY (from 3% to 8%), and the TOPO-capped sample went from 2% to 11%. Also checked was the effect of laser exposure on the CdSe nanorod cores capped with HDA. After overnight laser exposure, the HDA-coated CdSe nanorod cores experienced a degradation in their QY (from 4% to 2%).

All laser exposure experiments were repeated using the 457.9 nm laser line excitation. For the core/shell rods the QY versus photons absorbed per particle showed the same behavior as in the previous experiments, saturating after the same number of absorbed photons, whereas CdSe cores again experienced either no change or a decrease in QY. This indicates that the photoannealing process is not dependent on the excitation energy, just that the energy is absorbed by the nanocrystal. In all cases the QY of the photoannealed core/shells was unexpectedly surprisingly much higher than the initial, pre-annealing value. More importantly, this process is irreversible: all cleaned samples of photoactivated core/shell nanocrystals, left in the dark under Ar for months, did not increase or decrease their QY by significant amounts (less than 5% variation was considered to be within the experimental error). In addition there is no change in the fluorescence peak shape or peak maximum over this period of months. This is true for all of the surfactant-exchanged core/shells and core/shells that were washed with methanol at least once to remove any unreacted precursors, before photoannealing. The only sample that showed any change over time was the raw core/shell nanorods. After photoannealing, this sample underwent a very slow degradation process, most likely due to the presence of reactive species in the solution. Given the lower stability of raw core/shell nanorods, all quantitative studies were carried out on surfactant exchanged or cleaned core/shell samples.

IV. Photostability of the Core/Shell Rods

The solutions of photoactivated core/shell nanorods (obtained as described in the previous section) were opened to air and exposed again to laser light to check their stability against photooxidation. During these experiments, every nanocrystal in each sample absorbed approximately $3.5*10^9$ photons over 8 hours[50]. The HDA-capped sample showed the highest stability, with no change in QY and no blue shift in the luminescence peak. The HPA-capped and the TOPO-capped samples both experienced a blue shift of approximately 10 meV (4 nm) in their PL peak. The QY from the TOPO-capped sample slightly decreased (from 11% to 10%), whereas the PL from the HPA capped increased (from 8% to 14%). The corresponding cores oxidized more under the same conditions.

The growth of highly luminescent core/shell nanorods elucidates three basic concepts in interfacial growth: when both ZnS and CdS precursors are added, CdS preferentially grows first to reduce the interfacial energy; photoannealing permanently changes the core/shell nanorods, implying a structural reorganization; and growing shells on nanorods allows for the study of strain in a system that is intermediary between a "0D" nanocrystal core and a "2D" bulk surface.

Interfacial segregation is required for shell growth in this system, and yet CdS grows first on the CdSe core. Although the ratio of Zn:Cd injected is ~8:1, the ratio of ZnS:CdS in the first two monolayers of shell is only 2:1. As the shell thickness increases this ratio goes from 2:1 to 4:1 to ~4.5:1 and levels out as the shell thickness increases. The concentration of Zn in the precursor solution cannot compensate for the larger ZnS lattice mismatch, so initially Cd is more likely to stick to the surface of the CdSe cores. The farther away from the core (or the thicker the shell), the more the ratio depends solely on the concentration. When no Cd is added, the strain is so great that either no shell grows at all, or a tail of ZnS grows out one end of the nanorods.

This interfacial segregation could also be partially driven by the lower solubility of CdS with respect to ZnS in the surfactant used to grow the shell (TOPO). This concept, of selective precipitation has been used to grow CdS/HgS/CdS quantum dot/quantum wells in aqueous solvents due to the large difference in solubility products of $Cd^{2+}$ and $Hg^{2+}$, see Eychmuller, A. et al. Chem. Phys. Lett 1993, 208, 59-62. the contents of which are hereby incorporated herein by reference in its entirety for all purposes. While not wishing to be bound by any particular theory or principle, it is known that Cd atoms form less stable complexes with TOPO than Zn atoms do, and this may influence the order in which the atoms add to the core nanorod surface. If the shell growth were purely due to solubility differences, then it might be possible to grow a pure ZnS shell on CdSe core nanorods. However, this is not observed because the strain between CdSe and ZnS is too large. Therefore, while not wishing to be bound by any particular theory or principle, the inventors believe that the main mechanism responsible for the formation of graded shells in our system is strain-induced interfacial segregation.

In a typical synthesis of core/shell dots or nanocrystals, such as the CdSe/ZnS or the CdSe/CdS system, as the thickness of the shell increases, the luminescence QY first increases, and then declines. This trend is believed to be a consequence of increased strain in the shell. As long as the strain can be tolerated, the epilayer passivates the interface trap states and does not create additional mid-gap states. Once past a certain shell thickness, the strain is released through the formation of dislocations in the shell. Dislocations act as non-radiative recombination centers and lower the QY. In the present invention, the inventors noticed the same trend under normal conditions. However, the samples were irradiated with laser light, the QYs increased significantly: even samples with a thick irregular shell had a QY greater than 10% after this process.

The low luminescence observed in samples before laser irradiation indicates that a significant amount of non-radiative recombination centers are present throughout the shell. There is a permanent increase in QY of our core/shell nanorods, after laser irradiation, suggesting that the laser induces a structural reorganization in the shell. The laser power was kept low enough that the temperature of the solution remained constant. In addition, experiments were performed where solutions of core/shell nanorods were externally heated to 160° C. and the photoluminescence was monitored. Even after hours at this elevated temperature there was no increase in QY. This implies that a photochemical process is responsible for annealing the core/shells. Thermal annealing cannot be performed above the growth temperature of 160° C. since other processes such as Ostwald ripening or dissolution of the particles can occur.

Structural changes that lead to a permanent change in the luminescence QY of semiconductor dots or films are known to occur under high-power laser excitation, although there are known cases where these changes occur under photoexcitation. For instance, disordered ZnS:Mn films showed enhanced luminescence from $Mn^{2+}$ ions when irradiated by ultraviolet laser with energy pulses well below the conventional annealing threshold. This was explained by the low energy of formation and diffusion of defects in disordered semiconductors. Although in core/shell rods the evidence brought by TEM and XRD results can rule out a highly disordered shell, a certain number of defects are likely present at the highly strained interface. There is the possibility that chemical bonds at the interface can rearrange, or that defects can diffuse to the outer surface through a photochemically activated process. This is possible because the shell is only few nanometers thick. In addition, laser irradiation can induce surface reconstructions, which would decrease the number of surface trap states.

TEM, HRTEM, and XRD were performed on samples before and after photoannealing. There were no shape or structural changes observed using any of these methods. This is not surprising, however, considering the fact that all of these techniques rely on diffraction from planes of atoms, and are not sensitive to the positions of individual atoms. As borne out by simulations, see Wickham, J. N. et al. Phys. Rev. Lett. 2000, 84, 923-926, (the contents of which are hereby incorporated herein by reference in its entirety for all purposes, these techniques are not sensitive to the surface atoms or the individual atoms at the interface of the core/shell nanocrystals. Any structural changes occurring at the surface or interface would therefore not be observed.

The surfactant dependence of the core/shell QY can be understood by considering that in this system the carriers are not completely localized in the core and can sample the outer surface of the rod. This explains why some surfactants (long chain alkyl amines) increase the luminescence from core/shell nanocrystals by neutralizing surface trap states, whereas other molecules (such as pyridine) decrease it. Bulky surfactants, such as TOPO, are not able to passivate all the metal sites on the surface and are therefore less efficient than alkyl amines. A more uniform surface coordination, such as the one offered by alkyl amines, also imparts a higher stability against photooxidation. Although in our case, the addition of different surfactants leads to different initial and final QYs, the annealing process followed the same behavior as a function of incident photons. If the increase in QY were the result of the surfactant reacting with the surface of the shell then we would not observe the same behavior by different surfactants with different functional groups.

All of this evidence indicates that the photoannealing leads to a permanent change in the core/shell nanorods. Such a permanent change not only rules out photobrightening or oxidation as the cause of the increased QY, but also supports the theory that a structural rearrangement has occurred. Since there are no obvious changes observed in the HRTEM and XRD of the annealed sample, but the changes are permanent, the annealing is most likely only affecting the core/shell interface or the surface of the shell.

Core/shell nanorods provide a unique system for the study of strain in shell growth. Unlike in 2D epitaxial growth, the substrate (in this case the nanorod) is not fixed, so the lattice planes can actually be compressed by growth of the shell material. In addition, since this is a 1D system, some of the crystal faces behave more like those in a 2D system, while other faces behave more like the 0D surfaces of a highly curved spherical nanocrystal. The growth of shells with such a high lattice mismatch accentuates the induced strain and XRD provides a means to observe the strain induced by the CdS/ZnS shell. All of the diffraction peaks shift to lower d-spacings (higher 2θ) as a function of shell thickness. Upon shell growth, the 002 peak shifts the most of any of the 5 diffraction peaks (in all samples). Each plane in the (002) family of planes extends for only 3-4 nanometers. On the other hand, the 100 peak is generated by planes that are parallel to the c-axis. Each of these planes extends along the whole length of the rods, which is at least 3 to 8 times larger than the (002) planes in the nanorods. This peak shifts less than any other diffraction peak (in all samples) as a function of shell thickness. All of the other diffraction peaks shift by amounts that are intermediate between the shifts in the 002 and the 100 peaks. This implies that the planes extending along the diameter of the rod (or having a significant component along the diameter) are more compressed than planes extending along the length of the rod. This observation can be understood if one considers that, unlike traditional methods of shell growth where the substrate is fixed (bulk), the substrate in this case is thin enough that the shell can actually compress the lattice planes of the core. This compression of planes is more pronounced at their edges, near the core/shell interface. Since planes made up of very few atoms, such as the ones along the diameter of the rods, are more affected by this perturbation, their average d-spacing will change more than the extended planes with many atoms. These larger planes, such as the (100) planes, which extend along the length of the nanorod, may only be compressed at their ends, but not throughout the entire crystal length.

In addition, the intensity of the 002 peak decreases relative to the other peaks in the sample. This is not what one might expect since TEM analysis shows that the average length of the rods is increasing with shell thickness. The increase in length should make the 002 peak narrower and more intense as the domain size is increasing. Once we take into account the strain, however, these results make sense. As the compression of the 002 planes increases with shell thickness, this will cause a broader distribution of observed domain sizes, thereby spreading out the 002 peak and decreasing its intensity, while the other d-spacings, and therefore peaks are not affected as significantly.

TABLE 1

CdSe core nanorod growth conditions and corresponding average sizes.

| Rod length (nm) | Rod diameter (nm) | HPA (g) | TDPA (g) | TOPO (g) | Reaction time (min) |
|---|---|---|---|---|---|
| 18 | 5.0 | 0.04 | 0.456 | 3.50 | 5 |
| 23 | 3.3 | 0.13 | 0.34 | 3.55 | 2 |
| 21 | 3.3 | 0.08 | 0.39 | 3.53 | 4 |
| 36 | 4.5 | 0.13 | 0.34 | 3.55 | 5 |

TABLE 2

Core/shell nanorod growth conditions, final average sizes, number of shell monolayers and composition of the shell.

| Sample | mL of Stock Solution | Rod length (nm) | Rod diameter (nm) | # of Shell Monolayers | CdS in Shell | Zn:Cd in Shell |
|---|---|---|---|---|---|---|
| Core | 0 | 22.8 | 3.3 | 0 | 0% | NA |
| Thin Shell | 0.6 | 24.2 | 4.4 | 2 | 35% | 2:1 |
| Medium Shell | 0.75 | 27.0 | 6.0 | 4.5 | 22% | 4:1 |
| Thick Shell | 1.5 | 29.8* | 7.3 | 6.5 | 22% | 4.5:1 |

*The given length is the average "body" length and does not include the tail if present

TABLE 3

XRD peak changes as a function of shell thickness.

| Sample | 002 Peak Position | 002 d-spacing change | 100 Peak Position | 100 d-spacing change |
|---|---|---|---|---|
| Core | 29.6 | 0.0% | 28.1 | 0.0% |
| Thin Shell | 30.05 | 1.5% | 28.4 | 0.9% |
| Medium Shell | 30.35 | 2.4% | 28.6 | 1.5% |
| Thick Shell | 30.75 | 3.7% | 28.75 | 2.0% |

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention.

All patents, patent applications, and publications mentioned above are herein incorporated by reference in their entirety for all purposes. None of the patents, patent applications, and publications mentioned above are admitted to be prior art.

What is claimed is:

1. A graded core/shell semiconductor nanorod comprising:
   at least a first segment comprising:
   a core comprising a Group II-VI, Group III-V or a Group IV semiconductor, a graded shell overlying the core,
   wherein the graded shell comprises at least two monolayers,
   wherein the at least two monolayers each independently comprise a Group II-VI, Group III-V or a Group IV semiconductor.

2. The graded core/shell semiconductor nanorod of claim 1, wherein:
   the graded shell has at least three monolayers, and
   the monolayer closest to the core comprises a first semiconductor material, and
   the outermost monolayer comprises a second semiconductor material, wherein between the monolayer closest to the core and the outermost monolayer there exists a concentration gradient of the first and second semiconductor material.

3. The graded core/shell semiconductor nanorod of claim 1, wherein: the number of monolayers is between two and eight.

4. The graded core/shell semiconductor nanorod of claim 3, wherein: the number of monolayers is between 2 and 6.

5. The graded core/shell semiconductor nanorod of claim 1, wherein: there is a tail extending longitudinally from the core.

6. The graded core/shell semiconductor nanorod of claim 1, wherein:
the core comprises CdSe and the graded core/shell comprises CdS/ZnS.

7. The graded core/shell semiconductor nanorod of claim 1, wherein:
there is joined to the first segment a second segment comprising:
a core comprising a Group II-VI, Group III-V or a Group IV semiconductor,
a graded shell overlying the core,
wherein the graded shell comprises at least two monolayers,
wherein the at least two monolayers each independently comprise a Group II-VI, Group III-V or a Group IV semiconductor.

8. The graded core/shell semiconductor nanorod of claim 7, wherein:
the second segment core comprises CdSe and the second segment graded shell monolayers comprise, in order, CdS/ZnS.

9. The graded core/shell semiconductor nanorod of claim 8, wherein:
the first and the second segments have different cross sectional areas.

10. The graded core/shell semiconductor nanorod of claim 8, wherein:
there is a third segment joined to the second segment.

11. The graded core/shell semiconductor nanorod of claim 10, wherein:
the first, second and third segments have different cross sectional areas.

12. A nanorod barcode, comprising:
a first segment of a first material; and
a second segment of a second material joined longitudinally to said first segment;
wherein at least one of the first and second segments is configured to generate emission in response to excitation energy, and wherein:
said first and second segments comprise a nanorod core, and
said first and second segment cores independently comprise either a semiconductor material selected from the group consisting of Group II-VI, Group III-V and Group IV semiconductors or a metal selected from the group consisting of transition metals, oxides and nitrides thereof.

13. The nanorod barcode of claim 12, wherein:
said first and second segment cores independently comprise a semiconductor material selected from the group consisting of Group II-VI, Group III-V and Group IV semiconductors.

14. The nanorod barcode of claim 12, wherein:
said first segment core comprises a metal selected from the group consisting of transition metals, oxides and nitrides thereof, and
said second segment comprises a semiconductor material selected from the group consisting of Group II-VI, Group III-V and Group IV semiconductors.

15. The nanorod barcode of claim 12, further comprising:
a third segment connected longitudinally to said first segment core, and
said third segment core comprising a semiconductor material selected from the group consisting of Group II-VI, Group III-V and Group IV semiconductors.

16. The nanorod barcode of claim 15, wherein:
said second and third segments have different cross sectional areas.

17. The nanorod barcode of claim 15, wherein:
said first segment core comprises Co, and said second and third segment cores comprise CdSe.

18. The nanorod barcode of claim 13, wherein:
said first and second segments have different cross sectional areas.

19. The nanorod barcode of claim 18, wherein:
at least one of said first and second segment cores has a graded shell overlying the core.

20. The nanorod barcode of claim 18, wherein:
both segment cores have a graded shell overlying said cores.

21. The nanorod barcode of claim 13, wherein:
there is a third segment joined longitudinally to said second segment, and
said third segment comprises a semiconductor material selected from the group consisting of Group II-VI, Group III-V and Group IV semiconductors.

22. The nanorod barcode of claim 21, wherein:
at least one of said first and second and third segment cores has a graded shell overlying the core.

23. The nanorod barcode of claim 22, wherein: all segment cores have a graded shell overlying the cores.

24. The nanorod barcode of claim 15, wherein:
said first, second and third segments have different cross sectional areas.

25. A method of using a nanorod barcode to identify an element, comprising:
labeling at least one identifiable element with at least one nanorod barcode as claimed in claim 12.

26. The graded core/shell semiconductor nanorod of claim 1, wherein:
the core comprises CdSe and the graded core/shell comprises CdS/ZnS, and wherein a concentration of ZnS in the graded core shell gradually increases from the core outward.

* * * * *